United States Patent [19]

Gottlieb

[11] 4,167,945

[45] Sep. 18, 1979

[54] METHOD FOR ENHANCING THE HEALING OF GRAFTED TISSUE

[76] Inventor: Sheldon K. Gottlieb, 8708 Wandering Trail Dr., Potomac, Md. 20854

[21] Appl. No.: 857,527

[22] Filed: Dec. 5, 1977

Related U.S. Application Data

[63] Continuation-in-part of Ser. No. 764,229, Jan. 31, 1977, Pat. No. 4,061,731, which is a continuation-in-part of Ser. No. 576,858, Jun. 4, 1975, Pat. No. 4,006,220.

[51] Int. Cl.² .................... A61B 17/04; A61B 19/00; A61K 31/195; A61K 37/00
[52] U.S. Cl. .................... 128/334 R; 128/1 R; 128/156; 424/101; 424/177; 424/319
[58] Field of Search ............ 128/334 R, 1 R, 156; 424/101, 177, 319

[56] References Cited

U.S. PATENT DOCUMENTS

| | | | |
|---|---|---|---|
| 2,939,817 | 6/1960 | Nagasawa et al. | 128/1 R X |
| 3,223,083 | 12/1965 | Cobey | 128/334 R |
| 3,741,204 | 6/1973 | Thiele | 128/334 R X |
| 3,875,937 | 4/1975 | Scmitt et al. | 128/156 |
| 4,016,877 | 4/1977 | Cruz et al. | 128/156 |
| 4,066,083 | 1/1978 | Ries | 128/334 R X |
| 4,089,333 | 5/1978 | Utsuo et al. | 128/156 |

OTHER PUBLICATIONS

U.S. Dispensatory, 25th. Ed., 1955, Lippincott, Phila., pp. 1541–1543, cited.

*Primary Examiner*—Robert E. Bagwill
*Attorney, Agent, or Firm*—Schwartz & Weinrieb

[57] ABSTRACT

Method for grafting of a surface of donor tissue to a recipient tissue surface comprising the steps of coating freshly exposed recipient tissue surface with a composition consisting essentially of a connective tissue growth-promoting agent which is pulverized absorbable gelatin sponge, aminocaproic acid, compounds of the formula $4NH_2CH_2(CH_2)_4COOX \cdot CaX_2$ wherein X is chloride or bromide or mixtures thereof. Donor tissue is then placed onto the recipient surface whereby said composition forms an interface between the donor tissue surface and the surface of the recipient tissue.

11 Claims, No Drawings

METHOD FOR ENHANCING THE HEALING OF GRAFTED TISSUE

This application is a continuation-in-part of my copending application, Ser. No. 764,229, filed Jan. 31, 1977, now U.S. Pat. No. 4,061,731 said application being a continuation-in-part of my copending application Ser. No. 576,858, filed June 4, 1975, now U.S. Pat. No. 4,006,220.

BACKGROUND OF THE INVENTION

This invention relates to a method for promoting the rapid healing of grafted tissue and more particularly to a method for grafting a donor tissue surface to a recipient tissue surface. More particularly, the method of this invention is useful in encouraging the rapid healing of grafted tissue such as human autografts to repair ulcers, burns and male pattern alopecia.

In the past, considerable time on the order of several weeks would be required to pass before it was possible to determine if a particular full thickness or split thickness graft achieved a "positive take" condition. In addition, from 1 to 10 or more months would have to pass before the edges of the transplanted donor tissue would blend in with the surrounding tissue.

When donor plugs containing hair are transplanted, permanent hair growth usually does not take place for at least about 3 or 4 months after the transplant.

A need has therefore existed for a new method to achieve a "positive take" condition when donor tissue is grafted to a recipient tissue surface in a shorter period of time than has been possible heretofore. A need has also existed, in hair transplant technology, to achieve permanent hair growth in a shorter period of time.

OBJECTS OF THE INVENTION

It is therefore a principal object of the present invention to encourage the rapid healing of grafted donor tissue onto a recipient tissue surface.

Consistent with the primary object of the invention is the provision of a process that is more efficient, beneficial, and cosmetically acceptable for grafting donor tissue onto recipient tissue surfaces.

A further object of the present invention is the provision of a process whereby it appears possible to achieve permanent hair growth in a shorter time period than previously possible when tissue plugs containing hair are grafted into a freshly created cavity adapted for receiving said tissue plugs.

A still further object of this invention is the apparent uniting of opposed surfaces of graft and donor tissues in a considerably shorter period of time than was possible heretofore.

The invention will be better understood and objects other than those set forth herein will become apparent when consideration is given to the following detailed description and the illustrative embodiments discussed herein.

BRIEF SUMMARY OF THE INVENTION

Briefly, the present invention relates to a method for grafting donor tissue to recipient tissue. The method comprises the steps of coating the freshly exposed recipient tissue surfaces with a composition consisting essentially of a connective tissue growth-promoting agent selected from the group consisting of: (1) pulverized absorbable gelatin sponge, (2) aminocaproic acid, (3) a compound of the formula $4NH_2CH_2(CH_2)_4COOH \cdot CaX_2$ wherein X is chloride or bromide, or (4) mixtures thereof. The donor tissue is inserted onto the recipient surface whereby the composition forms an interface between the donor tissue and recipient tissue. This method promotes the build-up of new connective tissue thereby unifying more rapidly both the donor and recipient tissues.

DETAILED DESCRIPTION OF THE INVENTION

The process of the present invention is particularly useful for grafting donor tissue to a recipient tissue surface wherein the recipient tissue surface is essentially a cavity having exposed bottom and side wall surfaces. The types of cavities treated in accordance with this invention include both denuded and/or ulcerated tissue usually resulting from an injury to epithelial tissue. Where grafting is desired at a particular situs, e.g., to improve the cosmetic appearance of an individual, it is generally necessary to initially form a cavity within the desired recipient tissue surface. These cavities can be formed with an Orentreich punch or any conventional, e.g., (biopsy-type) punch. Such cavities are generally required in cosmetic surgery in the treatment of male pattern alopecia whereby a donor tissue plug containing hair is inserted into a freshly formed cavity having substantially the same dimensions as the plug. The plug is often 0.25 to 0.5 mm smaller in diameter than the diameter of the cavity.

The cavities formed for the insertion of donor plugs as part of a hair transplant procedure generally have a diameter of approximately 3 mm. to about 5 mm. Cavities formed with a punch generally have a depth of about 3 mm. to about 10 mm.

Once the wound is formed with a punch or by injury to the epithelial tissue, the composition defined hereinbefore is applied to the exposed recipient surface to form an interface between said recipient surface and the surface of the donor tissue. Generally, said composition is used in an amount sufficient to promote the build-up of new connective tissue between said donor tissue and said recipient tissue. Generally, the composition is applied in an amount to provide a coating having a thickness of between about 1 mm. to 5 mm.

The compositions used in the process of the invention are used in combination with human blood plasma. The plasma is preferably of human origin and preferably from the same patient being treated in accordance with the process of this invention. The plasma can be initially admixed with the composition, or the blood containing plasma can be permitted to flow into the cavity when said cavity is produced by injury or by means of a conventional punch.

As noted hereinbefore, the compositions used in the process of this invention contain either pulverized absorbable gelatin sponge or aminocaproic acid or the combination of these two materials. Thus, the compositions contain from about 0 to 50 mg., generally between about 5 and 50 mg. and preferably between about 30 and 40 mg. of pulverized absorbable gelatin sponge which is proteolytically digestable. The composition also contains from 0 to 75 mg., generally between about 12.5 to 75 mg. and preferably between about 30 and 40 mg. of aminocaproic acid which is preferably epsilon aminocaproic acid or the aminocaproic acid compounds as defined hereinbefore. The amounts set forth herein for both said sponge and aminocaproic acid are for each maximum of 0.5 cc., and preferably for each 0.3 to 0.5 cc. of plasma introduced into said cavity. As an optional ingredient, finely divided collagen may also be employed in an amount effective to promote the build-up of new collagen and is generally present in an amount between 5 and 50 mg., and preferably between 20 and 30 mg. for each maximum of 0.5 cc. of plasma introduced into the cavity.

When necessary, a pharmaceutically inert carrier can be used in combination with the composition. Examples of such carriers include water or saline solution.

It is further understood that the source of plasma, if introduced, is preferably obtained from either a sample of blood from the patient or from the blood plasma flowing into the cavity immediately after the formation thereof, such as in a fresh surface wound or cavity created with a punch. The plasma may also result from a combination of the two sources. It is the plasma fibrinogen and the thrombin located in the cavity of the injured tissue that react and ultimately result in the formation of fibrin which is replaced by fibroblasts required for the build-up of new connective tissue resulting in the rapid healing of grafted donor tissue onto a recipient tissue surface.

When plasma is used from a blood sample already removed from the patient, it is desirable to obtain said plasma by taking 15 cc. of the patient's venous blood and mixing the same with 2.3 cc. of anticoagulant citrate dextrose and thereafter centrifuging at 2000 revolutions per minute for 10 minutes. The clear plasma is then collected in a sterile test tube for its subsequent use.

Plasma obtained in this manner, or by other conventional procedures, may be either used immediately in the practice of this invention or may be stored for future use, such as in a refrigerator, with conventional additives optionally being incorporated into said plasma to aid in the preservation thereof, which need not be removed for the subsequent use of the plasma in the practice of this invention.

It is noted that donor tissue can also be in the form of a pinch graft. For example, if the recipient tissue surface is the exposed surface of an ulcer, the donor tissue grafted thereto can be in the form of a pinch graft.

What is claimed is:

1. A method for the grafting of a surface of donor tissue to a recipient tissue surface comprising the steps of:

coating freshly exposed recipient tissue surface with a composition consisting essentially of a connective tissue growth-promoting agent selected from the group consisting of: (1) pulverized absorbable gelatin sponge, (2) aminocaproic acid, (3) a compound of the formula $4NH_2CH_2(CH_2)_4COOH \cdot CaX_2$ wherein X is chloride or bromide, or (4) mixtures thereof; and placing said donor tissue onto said recipient surface whereby said composition forms an interface between said donor tissue surface and said recipient tissue surface, and said composition promotes the build-up of new connective tissue thereby unifying more rapidly said donor and recipient tissues.

2. The method of claim 1 wherein said composition further comprises plasma in an amount to provide sufficient fibrin to promote the build-up of new connective tissue.

3. The method of claim 2 wherein said composition contains from about 5 to 50 mg. of said pulverized absorbable gelatin sponge for each 0.3 to 0.5 cc of plasma.

4. The method of claim 2 wherein said composition contains from about 12.5 to 75 mg. of aminocaproic acid for each 0.3 to 0.5 cc. of plasma.

5. The method of claim 2 further comprising the step of initially forming a cavity having exposed surfaces to receive said donor tissue.

6. The method of claim 5 comprising forming a circular cavity having a diameter of about 3 mm. to 5 mm. and a depth of up to about 10 mm.

7. The method of claim 6 wherein said composition contains from about 5 to 50 mg. of said pulverized absorbable gelatin sponge for each 0.3 to 0.5 cc. of plasma introduced into said cavity.

8. The method of claim 7 comprising coating the exposed surfaces of said cavity with said composition in an amount sufficient to provide a coating thickness of between about 1 mm. and 5 mm.

9. The method of claim 7 wherein said composition further comprises between about 5 and 50 mg. of finely divided collagen for each 0.3 to 0.5 cc. of plasma introduced into said cavity.

10. The method of claim 2 wherein said donor tissue is a pinch graft and the recipient tissue surface is the exposed surface of an ulcer.

11. The method of claim 2 wherein said donor tissue is a punch graft of donor scalp.

* * * * *